(12) United States Patent
Hopf et al.

(10) Patent No.: US 10,753,520 B2
(45) Date of Patent: Aug. 25, 2020

(54) CONNECTION SYSTEM HAVING A THREADED NUT

(71) Applicant: Fresenius Kabi Deutschland GmbH, Bad Homburg (DE)

(72) Inventors: Hans-Juergen Hopf, Zirndorf (DE); Michael Hopf, Zirndorf (DE); Norbert Kassal, Oberasbach (DE); Alexander Hopf, Nuremberg (DE)

(73) Assignee: FRESENIUS KABI DEUTSCHLAND GmbH, Bad Homburg (DE)

( * ) Notice: Subject to any disclaimer, the term of this patent is extended or adjusted under 35 U.S.C. 154(b) by 883 days.

(21) Appl. No.: 14/652,101

(22) PCT Filed: Dec. 12, 2013

(86) PCT No.: PCT/EP2013/076428
§ 371 (c)(1),
(2) Date: Jun. 12, 2015

(87) PCT Pub. No.: WO2014/090958
PCT Pub. Date: Jun. 19, 2014

(65) Prior Publication Data
US 2015/0308596 A1    Oct. 29, 2015

(30) Foreign Application Priority Data
Dec. 13, 2012  (DE) .................. 10 2012 112 212

(51) Int. Cl.
*F16L 21/08* (2006.01)
*B29C 45/00* (2006.01)
(Continued)

(52) U.S. Cl.
CPC ............. *F16L 21/08* (2013.01); *A61M 39/10* (2013.01); *B29C 45/00* (2013.01); *F16L 19/00* (2013.01);
(Continued)

(58) Field of Classification Search
CPC .. A61M 2039/1027; A61M 2039/1033; A61M 2039/1038; A61M 2039/1088;
(Continued)

(56) References Cited

U.S. PATENT DOCUMENTS

| 3,365,999 A | * | 1/1968 | Perlin | ................. B29C 45/2622 411/34 |
| 3,789,724 A | * | 2/1974 | Moran | .................. F16B 37/043 411/432 |

(Continued)

FOREIGN PATENT DOCUMENTS

| CN | 201836188 | 5/2011 | |
| DE | 8909924 U1 | * 6/1990 | ......... B29C 45/2622 |

(Continued)

*Primary Examiner* — Amber R Anderson
*Assistant Examiner* — Stacy N Lawson
(74) *Attorney, Agent, or Firm* — Douglas Denninger (57) ABSTRACT

The present invention relates to a connection system for components through which fluid flows in medicine and medical equipment, comprising a male connection cone (6, 30) and a threaded nut (7) least partially surrounding the connection cone (6) and having an internal thread (9), for captively connecting the male connection cone (6, 30) to a female receptacle of an additional component through which fluid flows. The invention is characterised in that the threaded nut (7) has radially circumferential through-holes (10) at least in some sections in the axial section of the circumferential jacket of the threaded nut and webs (11, 11') are formed adjacent to the through-holes in the circumferential jacket, sections of the internal thread (9) being arranged on the inside of said webs in relation to the circumferential jacket. Furthermore, the invention also relates to the production of the connection system and to its use.

10 Claims, 6 Drawing Sheets

(51) Int. Cl.
*A61M 39/10* (2006.01)
*F16L 19/00* (2006.01)
*B29L 23/00* (2006.01)

(52) U.S. Cl.
CPC .............. *A61M 2039/1027* (2013.01); *A61M 2039/1088* (2013.01); *B29B 2023/00* (2013.01); *B29L 2023/007* (2013.01); *F16L 2201/44* (2013.01)

(58) Field of Classification Search
CPC .............. A61M 39/10; A61M 39/1011; B29L 2023/007; F16L 19/00; F16L 21/08; F16L 2201/44; B29C 45/2622
USPC ..................... 285/291.2, 330, 390, 391, 393; 264/328.1; 137/625.47; 604/533, 535
See application file for complete search history.

(56) References Cited

U.S. PATENT DOCUMENTS

| | | | | |
|---|---|---|---|---|
| 4,554,962 | A | * | 11/1985 | Wright ................... B22D 15/04 164/132 |
| 4,600,344 | A | * | 7/1986 | Sutenbach .......... F16B 37/0842 411/435 |
| 4,633,932 | A | * | 1/1987 | Ferguson ............... B22D 15/04 164/131 |
| 5,286,067 | A | * | 2/1994 | Choksi .................. A61M 39/10 285/331 |
| 5,380,135 | A | * | 1/1995 | Anquetin ............ B29C 45/2622 411/38 |
| 2004/0116858 | A1 | * | 6/2004 | Heinz .................. A61M 5/5086 604/111 |
| 2006/0178627 | A1 | * | 8/2006 | Geiger ................ A61M 5/3134 604/111 |
| 2007/0297855 | A1 | * | 12/2007 | Gerlach .............. B29C 45/2622 403/408.1 |
| 2008/0004600 | A1 | * | 1/2008 | Kitani ................... A61M 39/10 604/533 |
| 2010/0278615 | A1 | * | 11/2010 | Gerlach .............. B29C 45/2622 411/437 |
| 2011/0015580 | A1 | * | 1/2011 | Stroup ............. A61M 5/16881 604/207 |
| 2011/0048540 | A1 | * | 3/2011 | Stroup ............. A61M 5/16881 137/1 |
| 2011/0266477 | A1 | * | 11/2011 | Stroup ............. A61M 5/16881 251/152 |
| 2012/0157914 | A1 | * | 6/2012 | Stroup .................. A61M 39/26 604/68 |
| 2012/0191029 | A1 | * | 7/2012 | Hopf .................. A61M 39/1011 604/7 |
| 2012/0192968 | A1 | * | 8/2012 | Bonnal .............. A61M 39/1011 137/454.2 |
| 2013/0167841 | A1 | * | 7/2013 | Sheffer ............. A61M 16/0816 128/202.27 |
| 2014/0171875 | A1 | * | 6/2014 | Poncon ................. A61M 5/344 604/192 |

FOREIGN PATENT DOCUMENTS

| | | | | |
|---|---|---|---|---|
| DE | 20302788 | U1 | * | 6/2004 ........ A61M 39/1011 |
| EP | 0303127 | A1 | * | 2/1989 ......... B29C 45/2622 |
| JP | 2000245851 | A | * | 9/2000 |
| JP | 2006280501 | A | * | 10/2006 |
| JP | 2014100347 | A | * | 6/2014 |
| WO | WO-2013123028 | A1 | * | 8/2013 ............ A61M 39/10 |

\* cited by examiner

CONNECTION SYSTEM HAVING A THREADED NUT

CROSS-REFERENCE TO RELATED APPLICATIONS

This application is a national phase filing under 35 USC § 371 of international application No. PCT/EP2013/076428 filed 12 Dec. 2013, which claims priority to German Application No. 10 2012 112 212.1 filed 13 Dec. 2012. The entire contents of each of the above-mentioned applications are incorporated herein by reference.

FIELD OF THE INVENTION

The present invention relates to a connection system for fluid connections as used, in particular, in medicine and medical equipment.

BACKGROUND OF THE INVENTION

Connection systems for fluid connections are known in the state of art and are, for example, used in the fields of medicine and medical equipment. The connection systems are used in the fields of infusion, artificial nutrition, with syringes and injection equipment, in transfusion and in the supply or transfer of various flow media, and as injection equipment in the context of medical and pharmaceutical devices, which inter alia also comprise several components.

In medicine, among other things absolute safety in the handling of syringes, infusion tubes, cannulae etc. is of the utmost importance. For this reason, in medical technology, the Luer principle or Luer lock principle has prevailed vis-à-vis previously common connection systems. Luer lock is a standardised connection system for cannulae, syringes and infusion tubes in the medical field.

In this design, a seal is achieved by a conical construction of the connection components (the so-called Luer cone). The internal cone of one connection side is also referred to as "female", and the external cone of the opposite side is referred to as "male". The cone has a standard gradient of 6%.

If, for the purpose of securing or locking the connection against inadvertent disconnection, the cone is supplemented by a threaded nut or union nut with a thread, the system is referred to as a Luer lock. The simpler version without a screw thread on the syringe nozzle is referred to as a Luer connector, Luer adapter or Luer slip.

The Luer lock system ensures compatibility among various manufacturers and is internationally recognised. Worldwide, the Luer lock connection has established itself for reversible connections of syringes, cannulae, infusion tubes, spinal needles and the like. This represents a great advantage, in particular in the context of international aid and disaster operations.

At the same time, however, the universality of the system is associated with a dramatic disadvantage and with resulting dangers. Because of its universal standardisation the Luer lock connection has inherent possibilities for mix-ups because the system is compatible for vascular applications (veins and arteries) and for spinal or peridural applications (spiral cord), partly also for enteral applications (e.g. feeding tubes) and respiratory applications (airways). Thus this connection technique basically does not prevent, for example, medication that has to be injected venously from erroneously being applied spinally (into the spinal fluid). Unfortunately, several cases of such mix-ups with fatal consequences have occurred.

Apart from the above, from the point of view of process technology the manufacture of the threaded nut or the union nuts, as they are used, inter alia, in the Luer lock system, is relatively expensive, because for the internal thread of the nut during the manufacture in plastic injection moulding, a tool that can be rotated out or folded out needs to be used. This results in a significant increase in tool costs and increased manufacturing expenditure. The disadvantage is particularly significant if a plural number of such threads are provided on one component.

BRIEF SUMMARY OF THE INVENTION

It is the object of the present invention to at least partly overcome the disadvantages known from the state of the art. This relates on the one hand to an increase in user safety, and on the other hand to simplification of the manufacturing process.

The object of the present invention is met by a connection system as disclosed herein. Preferred embodiments of the invention form part of the subordinate claims, in particular also the method for manufacturing these connection systems and their use in the fields of medicine and medical equipment.

The connection system according to the invention for components through which fluid flows in medicine and medical equipment comprises at least one male connection cone and a threaded nut at least partially surrounding this connection cone and having an internal thread (nut thread).

In this design the threaded nut is in particular used for captively connecting the male connection cone to a female receptacle of an additional component through which fluid flows. In particular the female receptacle comprises external projections that engage the internal thread of the threaded nut. By rotation of the male connection cone into the female receptacle the components are connected in a fluid-tight and captive manner.

According to the present invention in some sections the threaded nut has radially circumferential through-holes in the axial section of its circumferential jacket, as a result of which through-holes webs or web sections are formed in the circumferential jacket. According to the present invention, furthermore, the threaded nut comprises the sections of the internal thread on the inside of the above-described webs.

In this document the term "sections of the internal thread" refers, in particular, to the thread flanks of the corresponding screw threads which are arranged adjacent to the through-holes, i.e. on the inside of the webs or web segments. According to the present invention the flanks of the internal thread essentially extend parallel to the through-holes and are also limited to these regions or sections. This can correspondingly be provided on all the webs or web elements, or only on some of these webs or web sections.

According to the present invention the term "web" refers to a structural feature of the circumferential jacket which at least on one side is adjacent to the circumferential through-hole. Furthermore, these webs can also be adjacent to two through-holes, wherein this is not mandatory.

For a better understanding of the present invention it should be mentioned that inter alia the through-holes are due to the manufacturing process in which parts of the tool project through the outer jacket of the threaded nut, thus providing the mould for binding the internal thread on the inside of the threaded nut or union nut in the injection moulding process.

The internal thread, manufactured in this manner, of a threaded nut thus provides an advantage in that no tool or tool section arranged within the thread needs to be provided for its manufacture. By simple linear closing and opening of the injection moulding tool, including the slide gate that may be necessary, thus a mould for an internal thread is provided, by means of which thread the internal screw threads of the threaded nut can be produced. This type of manufacture is associated with an advantage in that no rotatable or fold-out tool components need to be used to form the internal thread, and thus the cycle times in the injection moulding process can be reduced. Furthermore, a reduction in weight and material savings in the manufacture of the product are achieved.

According to a further particularly preferred embodiment of the present invention, the internal thread of the threaded nut is a double thread or a triple thread. It should also be taken into account that according to a further particularly preferred embodiment for each screw thread at least two through-holes are provided that are, for example, arranged opposite each other at the circumference of the threaded nut.

If triple threads are used, the through-holes are arranged so as to be offset by 120 degrees from each other, wherein for each alignment and thread entrance at least one or two, in particular three, through-holes are provided that in the axial direction are arranged one above the other, with in each case a corresponding section of the internal thread being arranged on their inside.

According to a further particularly preferred embodiment of the present invention, the through-holes, which in sections are radially circumferential and which preferably on the inside adjoin sections of the internal thread, extend over a third, in particular over at least two thirds, of the circumference, wherein the calculation relates to a sum of the corresponding internal thread structures for each pitch height, i.e. for each 360 degrees. In this context it is also advantageous that either by way of the number of screw threads or the number of revolutions of the screw thread the desired strength or stability of the screw connection can be influenced. Thus an increase in the number of screw threads is not only associated with an increase in the "gripability" of the thread but also with an increase in the stability and strength of the connection with otherwise identical design. In this context the term "gripability" refers to the type of thread design that makes it easier for a user to connect the external thread of the female counterpart with the threaded nut. The "gripability" increases as the number of threads increases, because the possible number of receiving locations for the counterpart in the threaded nut increases.

Preferably, the corresponding internal thread sections, which are provided in the case of double, and in particular in the case of triple, threads, are arranged axially one behind the other corresponding to the pitch height of the screw thread used.

According to a further particularly preferred embodiment of the present invention, apart from the webs, which extend in the circumferential jacket, reinforcement braces are provided by means of which, in particular, the webs are supported in the region of the through-holes. It should be taken into account that the webs, which preferably on the inside comprise a thread section, can be of a relatively thin design and that in particular with the use of double-thread connection systems relatively large forces act on the thread section. In order to ensure that these forces can be safely absorbed, and in order to at least partly prevent breaking of the webs and thus of the thread sections, according to this particular embodiment the reinforcement braces are arranged in the region between the attachment points to the circumferential jacket. Consequently, in particular the forces acting when a counterpart is screwed in can better be absorbed and dissipated without the component breaking.

For example, the median distance to the circumferential jacket that adjoins in the radial direction can be a possible attachment point for the reinforcement braces, wherein the reinforcement braces extend preferably so as to be axially parallel to the connection cone arranged in the interior of the threaded nut. As an alternative to this, the connection braces can also be arranged at an acute obtuse angle to the webs, wherein this angle is preferably between 75° and 90°.

According to a further particularly preferred embodiment of the present invention the present connection system does not have the dimensions of the standardised Luer system but as a result of modification of the corresponding dimensions provides protection against any mix-up. This ensures that as a result of different design sizes, the present connection system is incompatible with the Luer system that is, for example, commonly used in medical applications. This ensures, in particular, that with the use of the present connection system, for example in the field of artificial nutrition, any mix-up with connection systems as used, for example, in the field of infusion or injection equipment, can be excluded. To this effect the external diameter of the internal thread comprises, in particular, a diameter that is greater than 7.83 mm and preferably greater than 7.83 mm and smaller than 20 mm. According to a further particularly preferred embodiment the external diameter of the internal thread is greater than 8 mm and smaller than 10 mm and is, in particular, approximately 9 mm.

Apart from the external diameter, according to a further particularly preferred embodiment, the pitch height of the internal thread can be modified from the dimension used in the Luer system; according to the present invention said pitch height is preferably greater than 1.3 mm, furthermore greater than 1.3 mm and smaller than 5 mm. According to a further particularly preferred embodiment the pitch height is, in particular, greater than 1.5 mm and smaller than 3 mm and particularly preferably between 1.8 mm and 2.5 mm.

According to a further particularly preferred embodiment of the present invention at least some parts of the connection system are made from a material selected from a group comprising duroplastics and thermoplastics and in particular polyphenylene sulfide, polypropylene, poly-1-butene, polyvinyl chloride, polyvinylidene chloride, polymethyl metaacrylate, polymethyl methacrylate, polyacrylonitrile, polystyrene, polysulfone, polyacetal, polyvinyl alcohol, polyvinyl acetate, ethylene vinyl acetate (EVA), mixtures comprising ethylene vinyl acetate and polyethylene, ethylene vinylacetate copolymer (EVAC) for example Elvax or Evatane, ionomers, fluorocarbon plastic, polyethylene, polyamide in particular a partially aromatic polyamide, polycarbonate, polyester, polyphenylene oxide, polysulfone, polyvinyl acetal, polyurethane, and chlorinated polyether, cellulose nitrate, cellulose acetate, cellulose ether, phenolic resin, urea resin, thiourea resin, melamine resin, alkyl resin, allyl resin, silicon, polyimide, polybenzimidazole, epoxy resin, casein plastic, crosslinked polyurethane, unsaturated polyester resin, antimicrobial or antiseptic material such as for example highly-porous silver, silver manufactured without ions, silver alloys and in particular microsilver, metalions-releasing compounds, materials free of bisphenol A for example Tritan, Terlux, acrylonitrile-butadiene-styrene, combinations thereof and the like.

According to a further particularly preferred embodiment of the present invention the threaded nut is non-rotatably connected to the connection cone, and in particular formed in one piece with the connection cone.

According to an alternative embodiment to the above the connection cone comprises a radially circumferential groove in which the nut thread is designed as a union nut and is rotatably arranged. To this effect the connection cone and this union nut are manufactured in separate process steps and are subsequently mechanically interconnected.

The object of the present invention is also met by an injection moulding method for the manufacture of a connection system as described above, wherein this method only comprises the manufacture of a connection cone with a non-rotatably connected threaded nut or union nut, as a single component.

To this effect the method comprises the closing of the mould to form at least the connection cone and/or the threaded nut or union nut, the subsequent retraction of a slide gate to form flow paths and spaces within the component, the injection of the plastic material, the cooling of the plastic material in the mould, the extension of the slide gates, and the opening of the mould for removing (demoulding) the plastic components.

With this method it becomes clear that contrary to the otherwise normally-used slide gates to form the flow paths, in other words in particular rotatable slide gates, nonrotational slide gates can be used to form the internal threads of the threaded nut or union nut because the formation of the internal threads is provided by way of the external shape of the tools. This provides the particularly preferred advantage in that additional rotary movements within the tool, in particular the slide gates, can be so that the mould can be implemented economically, in particular in the production of a multitude of corresponding internal threads in different positions of a connection system, for example with the use of multiway valves. In this design the economical manufacture results from shortening the cycle times in the injection moulding process. For example, the typical cycle time in the manufacture of union nuts is approximately 21 to 22 seconds in the injection moulding process, wherein before and after injection the corresponding thread slide gates need to be rotated in or out. In comparison to this, in the manufacture of the threaded nut or union nut according to the invention the cycle time can be reduced by approximately 4 to 5 seconds. Moreover, as a result of the simplified design of the mould the corresponding associated costs are reduced by up to 40%. For example, in the case of simple tools there is no need to provide additional equipment such as core pull devices.

Apart from the connection system and its method for manufacture, the present invention also relates to the use of the connection system for the manufacture of corresponding components through which fluid flows in medicine and medical equipment, for example infusion tubes or transfusion tubes, Y-connectors, multiway valves, multiple distributors, injection equipment such as syringes, access devices or similar, as well as combinations thereof.

Below, the invention is explained with reference to various exemplary embodiments in the use of the connection system in combination with three-way valves, wherein it is expressly stated that the invention is not limited to these exemplary embodiments. Instead, the scope of the present invention requires a broad interpretation of the connection system in terms of its use according to the invention, and that, in particular, modifications as they would be made by the average person skilled in the art for the purpose of adaptation to corresponding components are also within the scope of the present invention.

BRIEF DESCRIPTION OF THE DRAWINGS

The following are shown.

DETAILED DESCRIPTION OF THE PRESENTLY PREFERRED EMBODIMENTS

Figure 1A:
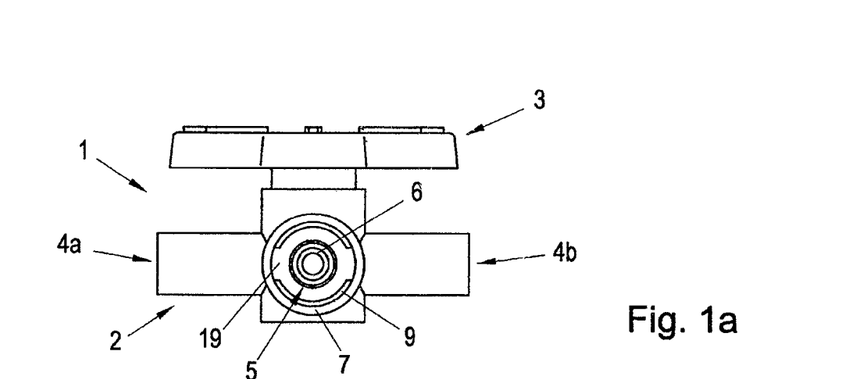
FIGS. 1a to 1c a three-way valve with a connection system according to the invention.
Figure 1B:
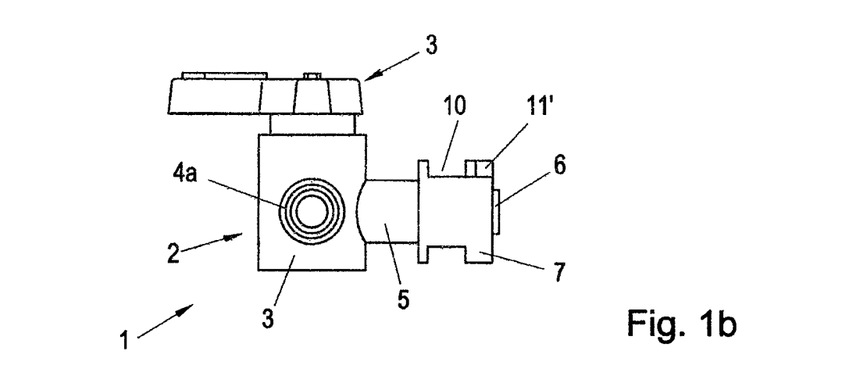
Figure 1C:
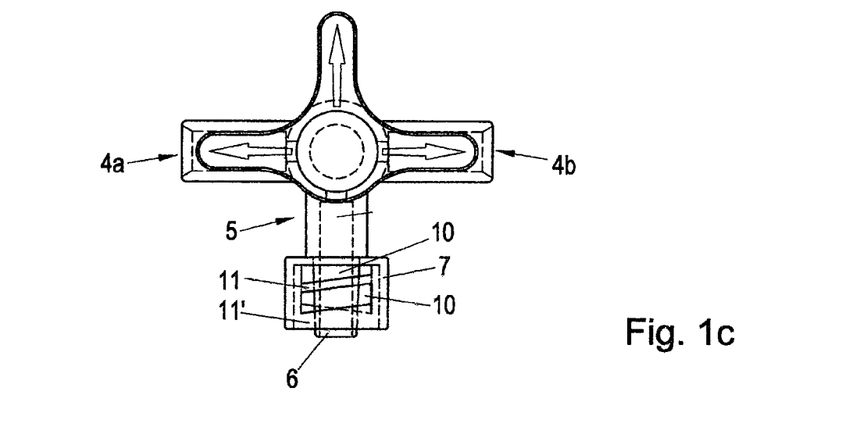

FIG. 1 shows a first embodiment of the connection system according to the invention in combination with a three-way valve 1. Apart from the housing 2 the plug 3 and the connection points 4a, 4b and 5 are shown. On the connection 5 the connection cone 6 with the threaded nut 7 is shown, wherein FIG. 1a in a lateral view apart from the circumferential jacket also shows the internal thread 9. According to the embodiment shown in the diagram, said internal thread 9 extends in each case by approximately 135 degrees so that on the right-hand side and on the left-hand side of the circumferential jacket spaces 19 result. The top view 1c clearly shows the through-holes 10 that determine the web 11 or the web section 11'. In FIG. 1b the three-way valve 1 with the connection system according to the invention is shown in a further lateral view, wherein here again in particular the through-holes 10 and the web section 11' are shown. In the embodiment shown, the threaded nut 7 is firmly connected to the connection cone 6 or to the connection point 5. To establish a connection with a female receptacle, the aforesaid is screwed into the nut 7 so that the male connection cone is received and is connected in a fluid-proof manner to the female receptacle (not shown).

Figure 2A:
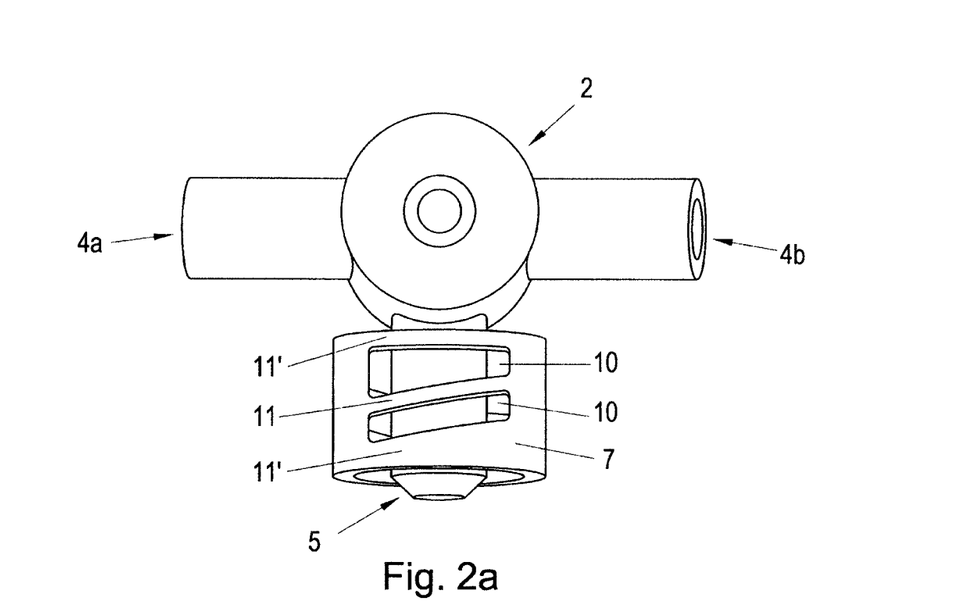
FIGS. 2a and 2b the three-way valve of FIG. 1 but without the plug.
Figure 2B:
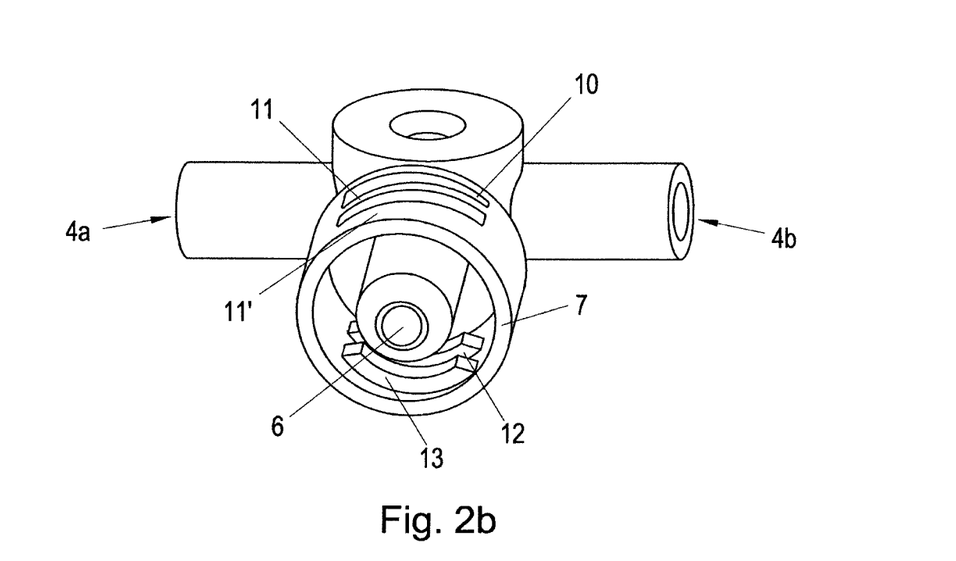

FIGS. 2a and 2b show a perspective view of the housing 2 with the threaded nut 7 according to the invention, wherein for the sake of clarity the plug is not shown. These illustrations again, apart from the connections 4a and 4b, show the connection 5 on which the threaded nut 7 is arranged. As already shown in FIG. 1c, said threaded nut 7 comprises the through-holes 10 and the web 11 or web section 11'. The component of FIG. 2b corresponds to the component of FIG. 2a, wherein in this illustration, in addition, the connection cone 6 is clearly shown. Furthermore, internally, the screw threads 12 and 13 are shown that extend on the inside adjacent to the through-holes 10.

Figure 3A:
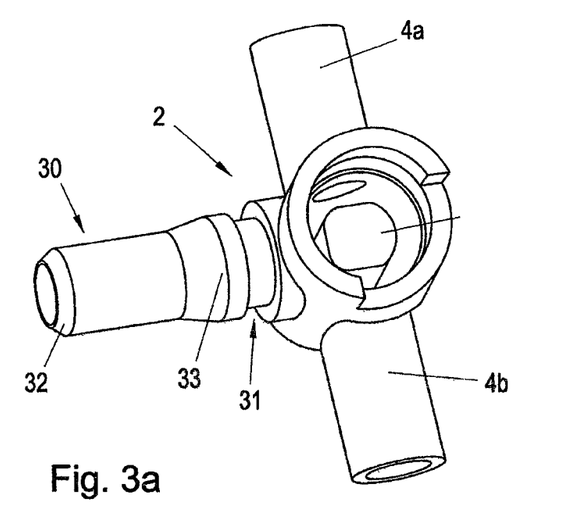
FIGS. 3a and 3b an alternative embodiment, in which the union nut is rotatably arranged in a further manufacturing step.
Figure 3B:
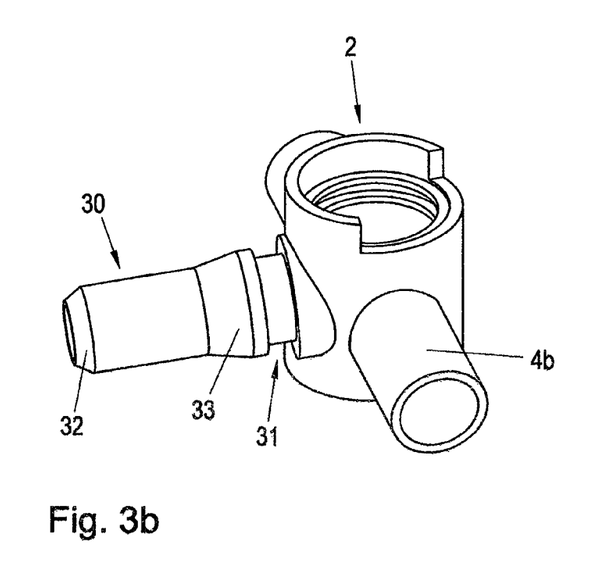

FIGS. 3a and 3b show an alternative embodiment of the arrangement of the connection system according to the invention, wherein in this embodiment a union nut (not shown) can be clipped onto the connection cone 30, which union nut can then correspondingly snaps into the circumferential groove 31. As a result of this joining of the two components a rotatable union nut is created which in particular provides an advantage in that the three-way valve, for example in the application for connecting the male connection cone 30 to a female receptacle (not shown), need not be rotated. The diagram shows particularly clearly that the connection cone 30 apart from the conical gradation 32 at the front end comprises a further conical thickening 33 that is used, in particular, in connection with the female receptacle, to provide a corresponding seal of the connection system. In this design preferably an embodiment of a union nut is selected as shown with reference to FIGS. 1 and 2, however, without the corresponding three-way valve but with a central aperture at the rear for receiving the connection point 30 and for clicking into the circumferential groove 31.

Figures 4A, 4B, 4C, 4D:
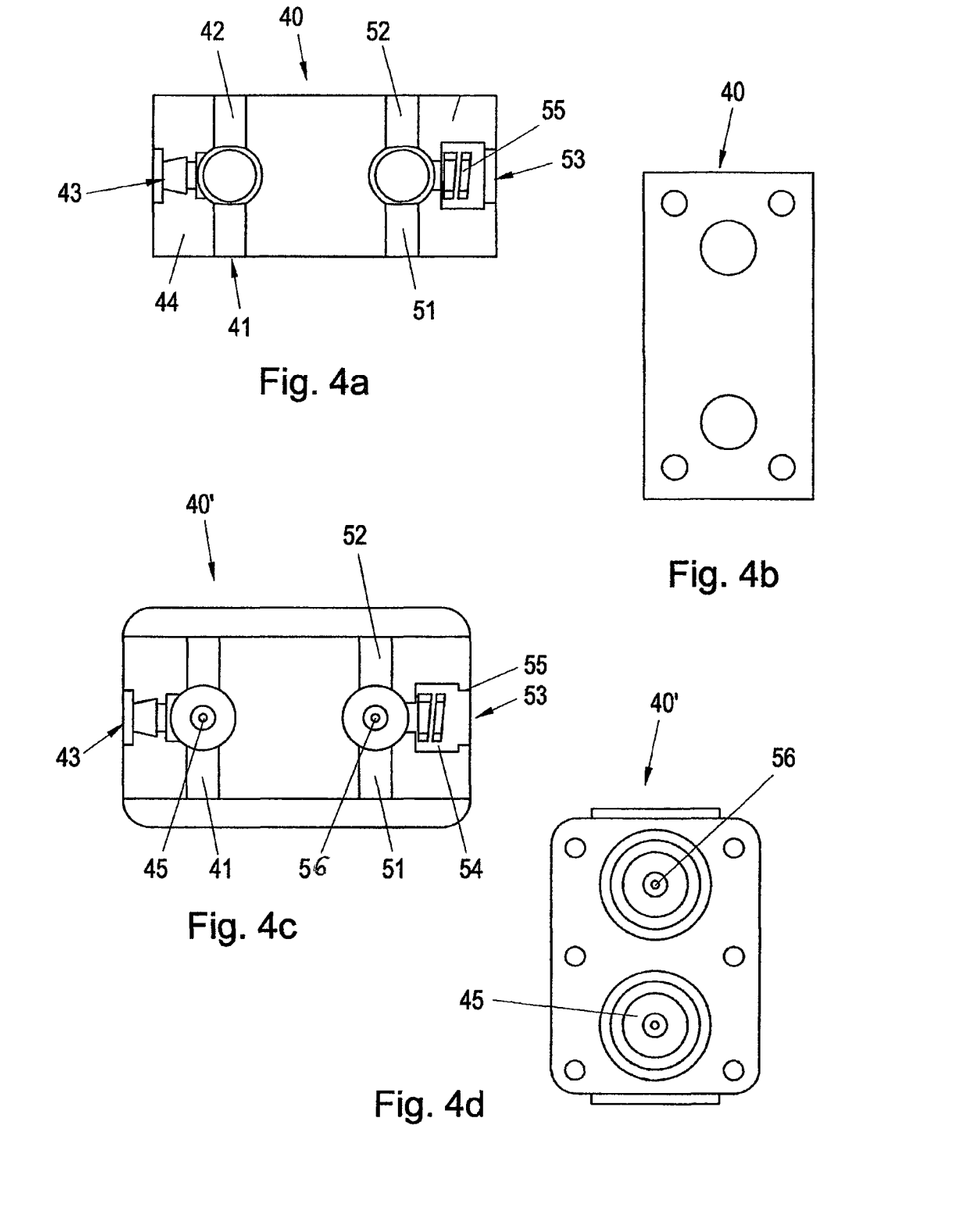
FIGS. 4a to 4d diagrammatic illustrations of the plastic injection moulding tools for manufacturing a three-way valve with a connection cone with and without a threaded nut.

FIGS. 4a to 4d show the two mould components 40 and 40' (4a and 4c: internal view; 4b and 4d: external view) for the manufacture of the connection system according to the invention in combination with a three-way valve, wherein apart from the recesses for the fluid connections 51 and 52 on the right-hand side the connection 53 is also shown, at which in conjunction with the connection cone by means of the projections 55 the jacket of the threaded nut is perforated and on the inside corresponding screw threads are produced. To this effect, during manufacture, a corresponding slide gate moves into the space of the connection 53, with the aforesaid forming the internal counterpart to the external mould. Analogously the same also applies to the fluid connections 51 and 52, which do not comprise a union nut or an internal screw thread. FIGS. 4c and 4d show the counterpart to the tool of FIGS. 4a and 4b, wherein apart from the corresponding component elements the injection points 45 and 56 are also shown. FIG. 4d shows the injection points on the rear of the tool.

According to the established method for the manufacture of such injection moulding components, in the injection moulding process the two components 4a/4b and 4c/4d are joined, thus forming the base body of the three-way valve with the threaded nut or union nut according to the invention. As a result of the insertion of corresponding slide gates (not shown) into the apertures 51, 52, 53 or 41, 42, 43 the spaces for the fluid paths are created. With this injection mould, furthermore, apart from producing the nut with the internal thread as described above, it is also possible to produce the three-way valve with a fixed threaded nut on the right-hand side and a three-way valve with a circumferential groove 44 for receiving or arranging a union nut on the left-hand side. Thus the embodiment shown in the diagram forms both alternatives of a connection system with a fixed threaded nut and a rotatable union nut, wherein the latter needs to be produced and arranged in at least one further manufacturing step.

Figure 5A:
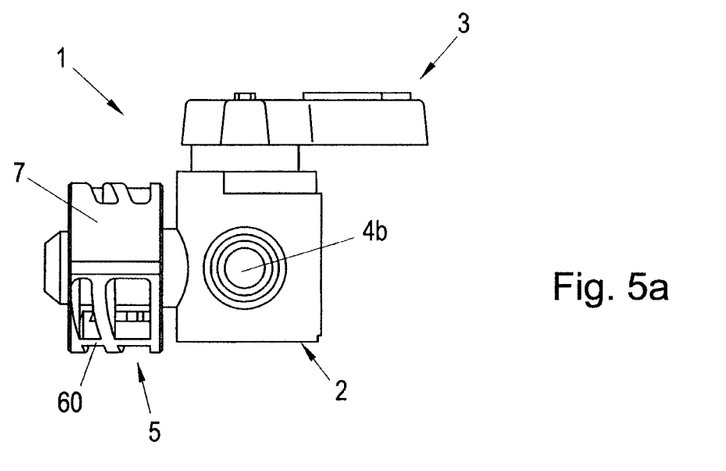
FIGS. 5a to 5e an alternative embodiment of the threaded nut with reinforcement webs.
Figure 5B:
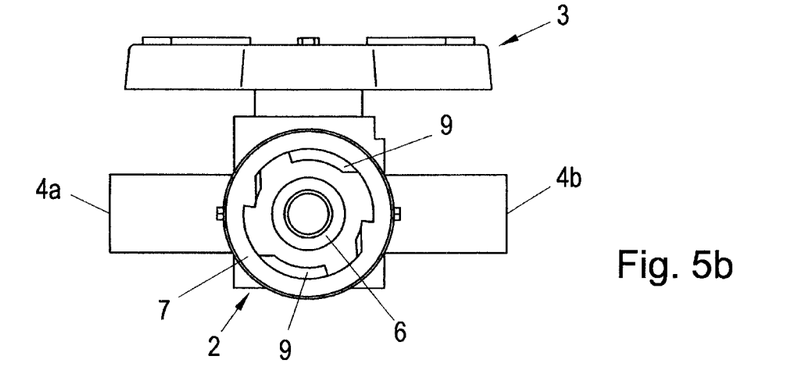
Figure 5C:
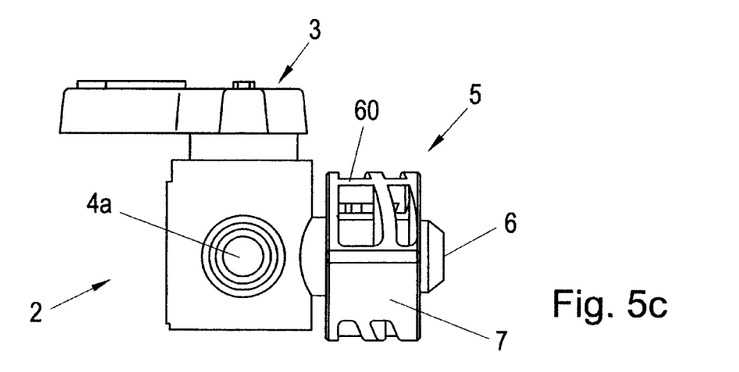
Figure 5D:
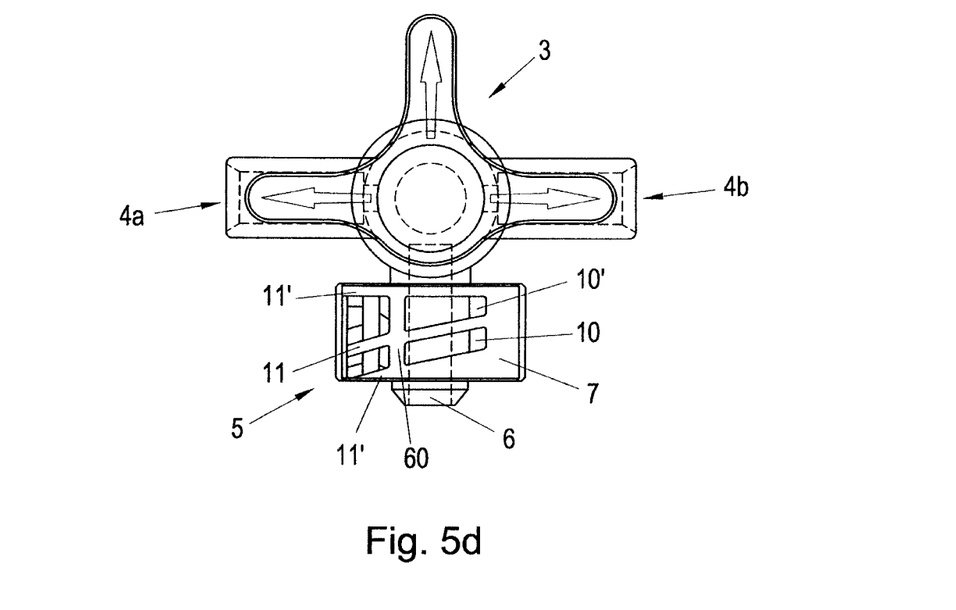
Figure 5E:
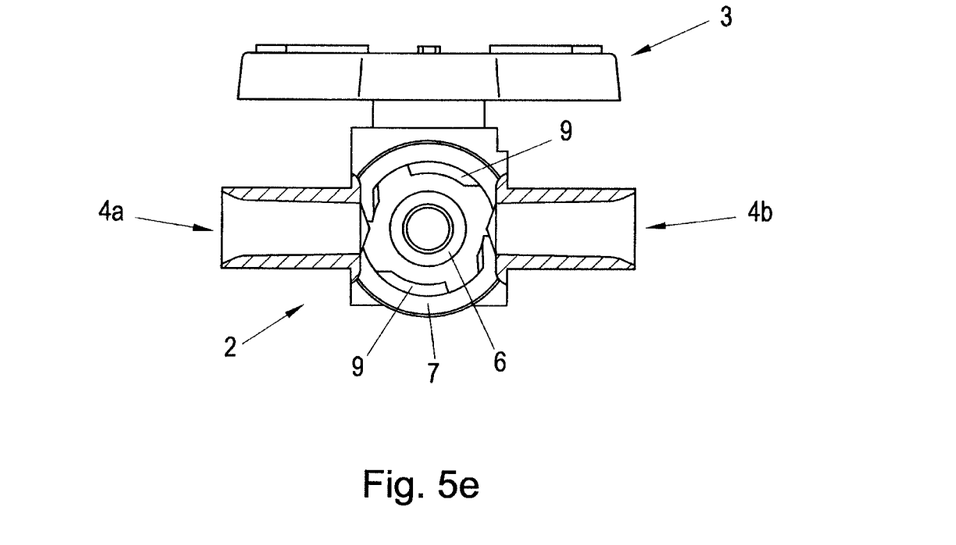

FIGS. 5a to 5e show a further embodiment of the present invention. Thus, FIG. 5a shows a lateral view from the right-hand side, FIG. 5b a front view, FIG. 5c a lateral view from the left-hand side, and FIG. 5d a top view. FIG. 5c shows a partial section view of the connection points 4a and 4b and the region of the threaded nut with the connection point 5. In this embodiment the radially circumferential webs 11 or 11' have been supplemented by means of reinforcement braces 60. These reinforcement braces, which in the present example are arranged so as to be parallel to the main direction of extension of the connection point 5, are used, among other things, to prevent any breaking of the thread when a female connector is screwed in. Thus, the female connectors or connection pieces are usually provided with circumferential segments or with two segments on the thread. Above all in the case of a double thread, the load on the thread section of the threaded nut is increased, and time and again breakage of the thread has been observed. The reinforcement braces shown in this exemplary embodiment can prevent such breaking, and therefore also provide the option of using female connectors/connection devices comprising various plastics (for example duroplastics and thermoplastics and in particular polyphenylene sulfide, polypropylene, poly-1-butene, polyvinyl chloride, polyvinylidene chloride, polymethyl metaacrylate, polymethyl methacrylate, polyacrylonitrile, polystyrene, polysulfone, polyacetal, polyvinyl alcohol, polyvinyl acetate, ethylene vinyl acetate (EVA), mixtures comprising ethylene vinyl acetate and polyethylene, ethylene vinylacetate copolymer (EVAC) for example Elvax or Evatane, ionomers, fluorocarbon plastic, polyethylene, polyamide in particular a partially aromatic polyamide, polycarbonate, polyester, polyphenylene oxide, polysulfone, polyvinyl acetal, polyurethane, and chlorinated polyether, cellulose nitrate, cellulose acetate, cellulose ether, phenolic resin, urea resin, thiourea resin, melamine resin, alkyl resin, allyl resin, silicon, polyimide, polybenzimidazole, epoxy resin, casein plastic, crosslinked polyurethane, unsaturated polyester resin, antimicrobial or antiseptic material such as for example highly-porous silver, silver manufactured without ions, silver alloys and in particular microsilver, metal-ions-releasing compounds, materials free of bisphenol A for example Tritan, Terlux, acrylonitrile-butadiene-styrene, combinations thereof and the like). Furthermore, in FIGS. 5a to 5e components that essentially correspond to the exemplary embodiments of the abovementioned designs have the same reference characters.

LIST OF REFERENCE CHARACTERS

1 Three-way valve
2 Housing
3 Plug
4a, 4b, 5 Connection points
6, 30 Male connection cone
7 Threaded nut
9 Internal thread
10 Through-holes
11, 11' Webs
12, 13 Screw threads
19 Space
30 Connection cone
31 Groove
32 Conical gradation
33 Thickening
40, 40' Mould components
41, 42, 43 Apertures
44 Circumferential groove
45 Injection gate
51, 52, 53 Fluid connections/apertures
53 Connection
55 Projections
56 Injection gate
60 Reinforcement brace

The invention claimed is:

1. A connection system for components through which fluid flows in medicine and medical equipment, the connection system comprising:
   a male connection cone; and
   a threaded nut including a circumferential jacket having an axial section at least partially surrounding the connection cone and having an internal thread, the threaded nut captively connecting the male connection cone to a female receptacle of an additional component through which fluid flows, the threaded nut having through-holes radially spaced about a circumference of the circumferential jacket in at least some portions of the axial section of the circumferential jacket, wherein webs are formed in the circumferential jacket adjacent to the through-holes, wherein sections of the internal thread are arranged on an inner surface of said webs in opposing relation to the through-holes and the internal thread sections are capable of being formed by projections of a mould through the through-holes opposing the internal thread sections, wherein the through-holes are at least as large as the opposing internal thread sections, wherein the internal thread sections are at least flanks of the internal thread, and wherein the internal thread sections are limited to regions of the webs;

wherein reinforcement braces are also formed in the circumferential jacket adjacent to the through-holes and the reinforcement braces are arranged at an angle to the webs; and wherein an edge of each of two of said through-holes is defined along one side of one of the reinforcement braces, with an edge of each of another two of said through-holes defined along another side of said one of the reinforcement braces.

2. The connection system according to claim 1, wherein the internal thread is a double thread or a triple thread.

3. The connection system according to claim 2, wherein for each thread of the double thread or the triple thread at least two through-holes are provided.

4. The connection system according to claim 1, wherein the radially spaced through-holes and/or sections of the internal thread extend over at least ⅓ of the circumference of the circumferential jacket.

5. The connection system according to claim 1, wherein at least one of (i) a maximum diameter of the internal thread is greater than 7.83 mm and smaller than 20 mm, and (ii) a pitch of the internal thread is greater than 1.3 mm and smaller than 5 mm.

6. The connection system according to claim 1, wherein at least some parts of the connection system are made from a material selected from a group consisting of duroplastics and thermoplastics and polyphenylene sulfide, polypropylene, poly-1-butene, polyvinyl chloride, polyvinylidene chloride, polymethyl metaacrylate, polymethyl methacrylate, polyacrylonitrile, polystyrene, polysulfone, polyacetal, polyvinyl alcohol, polyvinyl acetate, ethylene vinyl acetate (EVA), mixtures comprising ethylene vinyl acetate and polyethylene, ethylene vinylacetate copolymer (EVAC) ionomers, fluorocarbon plastic, polyethylene, polyamide, a partially aromatic polyamide, polycarbonate, polyester, polyphenylene oxide, polysulfone, polyvinyl acetal, polyurethane, and chlorinated polyether, cellulose nitrate, cellulose acetate, cellulose ether, phenolic resin, urea resin, thiourea resin, melamine resin, alkyl resin, allyl resin, silicon, polyimide, polybenzimidazole, epoxy resin, casein plastic, crosslinked polyurethane, unsaturated polyester resin, antimicrobial or antiseptic material, highly-porous silver, silver manufactured without ions, silver alloys and microsilver, metal-ions-releasing compounds, materials free of bisphenol A, Tritan, Terlux, acrylonitrile-butadiene-styrene, and combinations thereof.

7. The connection system according to claim 1, wherein the threaded nut is designed as a Luer lock component and is rotatably connected to the connection cone.

8. The connection system according to claim 1, wherein the connection system is capable of being used with infusion tubes, transfusion tubes, Y-connectors, multiway valves, multiple distributors, injection equipment, syringes, access devices, and combinations thereof.

9. An injection moulding method for the manufacture of a connection system, the method comprising:

selecting a mould configured to make a threaded nut including a circumferential jacket having an axial section configured to at least partially surround a male connection cone and having an internal thread, the threaded nut configured to captively connect the male connection cone to a female receptacle of an additional component through which fluid flows, the threaded nut having through-holes radially spaced about a circumference of the circumferential jacket in at least some portions of the axial section of the circumferential jacket, wherein webs are formed in the circumferential jacket adjacent to the through-holes, wherein sections of the internal thread are arranged on an inner surface of said webs in opposing relation to the through-holes and are formed by projections of the mould through the through-holes opposing the internal thread sections, wherein the through-holes are at least as large as the opposing internal thread sections, wherein the internal thread sections of the internal thread are at least the flanks of the internal thread, wherein the internal thread sections are limited to regions of the webs;

wherein reinforcement braces are also formed in the circumferential jacket adjacent to the through-holes and the reinforcement braces are arranged at an angle to the webs; and wherein an edge of each of two of said through-holes is defined along one side of one of the reinforcement braces, with an edge of each of another two of said through-holes defined along another side of said one of the reinforcement braces;

closing the mould;

injecting a plastic material;

cooling the plastic material in the mould; and opening the mould and demoulding the threaded nut having the internal thread sections formed by the projections of the mould through the through-holes opposing the internal thread sections.

10. A connection system for components through which fluid flows in medicine and medical equipment, the connection system comprising:

a male connection cone; and a threaded nut including a circumferential jacket having an axial section at least partially surrounding the connection cone and having an internal thread, the threaded nut captively connecting the male connection cone to a female receptacle of an additional component through which fluid flows, the threaded nut having through-holes radially spaced about a circumference of the circumferential jacket in at least some portions of the axial section of the circumferential jacket, wherein webs are formed in the circumferential jacket adjacent to the through-holes, wherein sections of the internal thread are arranged on an inner surface of said webs in opposing relation to the through-holes and the internal thread sections are capable of being formed by projections of a mould through the through-holes opposing the internal thread sections, wherein the through-holes are at least as large as the opposing internal thread sections, wherein the internal thread sections are at least flanks of the internal thread, and wherein the internal thread sections are limited to regions of the webs;

wherein reinforcement braces are also formed in the circumferential jacket adjacent to the through-holes and the reinforcement braces are arranged at an angle to the webs; and wherein two of said reinforcement braces, opposed to each other, extend axially along the circumferential jacket and an edge of each of two of said through-holes is defined along one side of each of the two reinforcement braces, with an edge of each of another two of said through-holes defined along another side of the respective reinforcement brace.

\* \* \* \* \*